(12) United States Patent
Geisler et al.

(10) Patent No.: US 6,653,491 B1
(45) Date of Patent: Nov. 25, 2003

(54) METHOD FOR PRODUCING 4,4-DIMETHYL-3β-HYDROXYPREGNA-8, 14-DIENE-21-CARBOXYLIC ACID ESTERS AND INTERMEDIATE PRODUCTS OBTAINED BY SAID METHOD

(75) Inventors: Jens Geisler, Berlin (DE); Eric Winter, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 09/936,910

(22) PCT Filed: Mar. 16, 2000

(86) PCT No.: PCT/EP00/02323

§ 371 (c)(1),
(2), (4) Date: Sep. 19, 2001

(87) PCT Pub. No.: WO00/56758

PCT Pub. Date: Sep. 28, 2000

(30) Foreign Application Priority Data

Mar. 19, 1999 (DE) .......................................... 199 14 019

(51) Int. Cl.[7] .............................. C07J 13/00; C07J 9/00
(52) U.S. Cl. ...................... 552/534; 552/530; 552/532; 552/544; 552/555
(58) Field of Search ................................. 560/122, 126, 560/128, 116; 552/552, 544, 530, 532, 539, 555

(56) References Cited

U.S. PATENT DOCUMENTS 5,384,313 A * 1/1995 DeLeuca et al.

FOREIGN PATENT DOCUMENTS

WO 9952930 10/1999

OTHER PUBLICATIONS

"Advanced Organic Chemistry", Jerry March, 3rd edition, John Wiely & Sons, Inc. 1985, p. 417.*
Blume et al, WO 99/52930, Oct. 21, 1999.*
Dolle R E et al: "Synthesis of Zymosterol, Fecosterol, and Related Biosynthetic Sterol Intermediates 1,2" Journal of The American Chemical Society, US, American Chemical Society, Washington, DC, Bd. 111, Nr. 1. Jan. 4, 1989 (Jan. 4, 1989), Seiten 278–284, XP000611665 ISSN: 0002–7863.
R B Woodard et al: "The Synthesis of Lanosterol (Lanostadienol)" Journal of The Chemical Society,GB,Chemical Society. Letchworth, Bd. 3, Nr. 3, Maerz 1957 (Mar. 1957), Seiten 1131–1144 1144, XP002111485.
Lettre et al: "Polyols derived from sterols and sterol derivatives. VI. Steroids containing structural units of ecdysone and the elatericins" Justus Liebigs Annalen der Chemie,de, Verlag Chemie GmbH. Weinheim, Bd. 758, Nr. 758, 1972, Seiten 89–110 110, XP002111484 ISSN: 0075–4617.

Wenckens M et al: "Synthesis of Meiosis–Activating Sterols Containing Fluorine" Acta Chemica Scandinavica,DK, Munksgaard, Copenhagen, Bd. 52, 1998, Seiten 503–507, XP000857743 ISSN: 0904–213X.

R E Dolle et al: "Improved Preparation of (3.beta.,5.alpha., 14.alpha.)–3–Hydroxy–14–m eth ylcholest–7–en–15–one. Synthesis of Ergostenone and 20.alpha.–(Hydroxymethyl-)pregnenone Analogues" Journal of Organic Chemistry,US, American Chemical Society. Easton, Bd. 51, Nr. 21, 17 Oktober 1986 (Oct. 17, 1986), Seiten 4047–4053–4053, XP002111486 ISSN:0022–3263.

J Van Der Eycken et al: "24(R),25–Dihydroxycholesterol;An Attempt for Side Chain Stereocontrol via Iodolactonization" Bulletin des Societes Chimiques Belges,GB,Pergamon Press Ltd. Oxford, Bd. 95, Nr. 4, Apr. 1986 (Apr. 1986), Seiten 289–292–292, XP002111487.

Ruan B et al: "An alternative synthesis of 4,4–Dimethyl–5alpha–cholesta–8,14,24–trie n–3beta–ol, an intermediate in sterol biosynthesis and a reported activator of meiosis and of nuclear orphan receptor LXRalpha" Bioorganic & Medicinal Chemistry Letters,GB,Oxford, Bd. 8, Nr. 3, Feb. 3, 1998 (Feb. 3, 1998), Seiten 233–236, XP004136854 ISSN: 0960–894X.

* cited by examiner

Primary Examiner—Johann Richter
Assistant Examiner—Paul A. Zucker
(74) Attorney, Agent, or Firm—Millen, White, Zelano & Branigan P.C.

(57) ABSTRACT

The invention relates to a method for representing compounds of the general formula (1). The invention further relates to the hitherto unknown compounds of general formulas (5, 6 and 7) in the form of intermediate products and to the use of 4,4-dimethyl-3β hydroxypregna-8,14-diene-21-carboxylic acid esters of the general formula (1) for producing 4,4-dimethyl-5α-cholesta-8,14,24-triene-3β-ol (2).

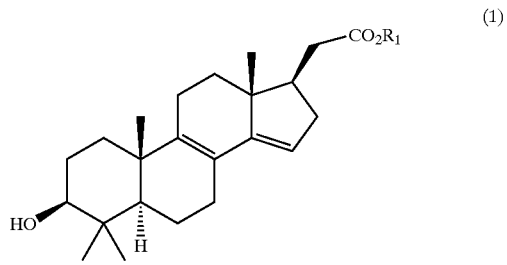

7 Claims, No Drawings

METHOD FOR PRODUCING 4,4-DIMETHYL-3β-HYDROXYPREGNA-8, 14-DIENE-21-CARBOXYLIC ACID ESTERS AND INTERMEDIATE PRODUCTS OBTAINED BY SAID METHOD

This application is a 371 of PCT/EP00/02323 filed Mar. 16, 2000.

The invention relates to a process for the production of 4,4-dimethyl-3β-hydroxy-pregna-8,14-diene-21-carboxylic acid esters (1) and intermediate products in the process

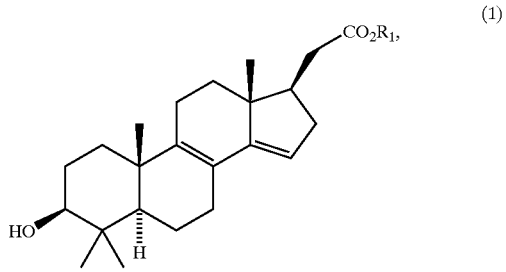

(1)

in which $R^1$=hydrogen, branched or unbranched $C_1$–$C_6$ alkyl, phenyl, benzyl, ortho-, meta- or para-methylphenyl, and the use for the production of 4,4-dimethyl-5α-cholesta-8,14,24-trien-3β-ol (2) (FF-MAS)

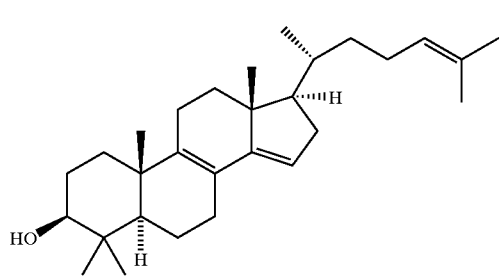

(2)

Studies by Byskov et al. (Nature 1995, 374, 559) show that 4,4-dimethyl-5α-cholesta-8,14,24-trien-3β-ol, formula 2, mentioned in the FF-MAS below and isolated from human follicular fluid, is an endogenous substance that regulates meiosis, to which advantageous hormonal effects are ascribed. This substance is thus important for pharmaceutical applications, for example for promoting fertility.

A first synthesis of this natural substance, which will take place in the biosynthesis of cholesterol from lanosterol, was described by Dolle et al. (J. Am. Chem. Soc. 1989, 111, 278). Starting from ergosterol, FF-MAS is obtained in an 18-stage resource-intensive synthesis sequence. Large portions of the synthesis are devoted to the chemical partial degradation of the ergosterol side chain, the subsequent creation of the FF-MAS side chain and the protective group chemistry that is necessary for achieving this goal.

A second synthesis of FF-MAS was described by Schroepfer et al., starting from dehydrocholesterol in a 13-stage synthesis (Bioorg. Med. Chem. Lett. 1997, 8, 233). Also in this synthesis, an resource-intensive protection of the diene system must be performed for the creation of a side-chain. Only four steps (epoxidation and rearrangement for protection; reduction and elimination for regeneration of the diene system) are due to the protective group strategy.

A third synthesis of FF-MAS was developed by Ruan et al. (Med. Chem. Letters 1998, 233). In this case, FF-MAS is built up starting from cholesterol in a 15-stage synthesis. Here, large portions of the synthesis are devoted to the resource-intensive build-up of the double-bond system in the steroid and the creation of the side-chain.

Additional processes are described within the still unpublished DE 198 17 520 and 198 23 677. These syntheses start from 3-oxopregn-4-ene-21-carboxylic acid esters. Central intermediate products of these processes are the 4,4-dimethyl-3β-hydroxypregna-8,14-diene-21-carboxylic acid esters that are described under general formula 1.

The object of this invention are new processes for the synthesis of these central intermediate stages. Also subjects of this invention are the new, previously unknown intermediate products that will be within the context of syntheses and can be used per se or derivatized as starting materials for the synthesis of other target molecules, for example for the synthesis of FF-MAS analogs (see WO 96/00235) and the use of compounds for the production of 4,4-dimethyl-5α-cholesta-8,14,24-trien-3β-ol.

This object is achieved by the teaching of the claims.

By the process according to the invention, there will be fewer intermediate stages than in the known syntheses from the prior art, and the number of purification steps is considerably lower.

Process According to the Invention

According to Diagram 1, 4,4-dimethyl-3β-hydroxypregna-8,14-diene-21-carboxylic acid esters of general formula 1 are produced in a 5-stage sequence starting from androstenedione (3).

The androstenedione that is used as starting material is commercially available.

Diagram 1

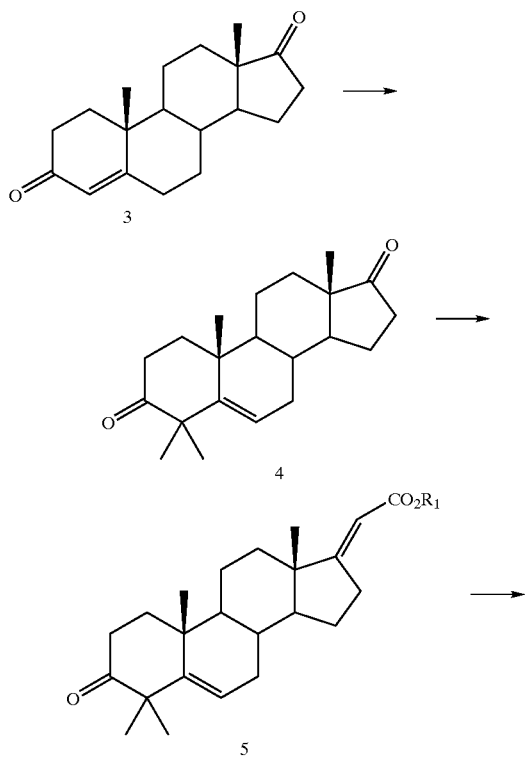

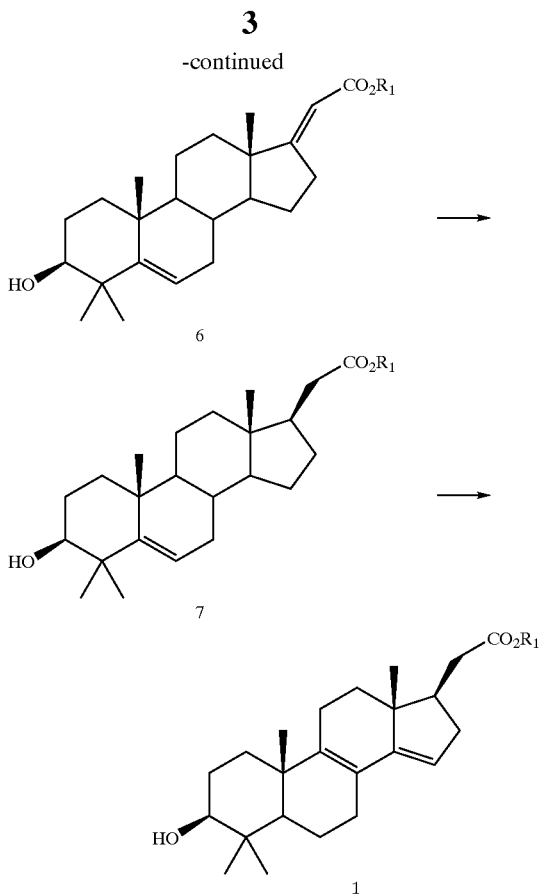

The reaction of a compound of formula 3 to form a compound of formula 4 is carried out according to processes that are known in the art (e.g., Helv. Chim. Acta 1980, 63, 1554; J. Am. Chem. Soc. 1954, 76, 2852). For example, a compound of formula 3 is reacted in the presence of bases, such as, for example, the alkali salts of lower alcohols, but preferably potassium tert-butylate with an alkylating agent, such as, for example, dimethyl sulfate, dimethyl carbonate or else methyl iodide in a solvent or solvent mixture. As solvents, lower alcohols, preferably tertiary alcohols as well as ethers, for example methyl tert-butyl ether, or tetrahydrofuran and mixtures thereof can be used. Preferred is the use of tert-butanol or a mixture that consists of tert-butanol and tetrahydrofuran. The reaction is performed in a temperature range of 0° C. to 65° C., but preferably in a temperature range of 15° C. to 50° C.

The reaction of a compound of formula 4 to form a compound of formula 5 is carried out according to processes that are known in the art (e.g., Synth. Commun. 1977, 7, 215; JOC 1988, 3947; J. Prakt. Chem. 1990, 367). For example, a compound of formula 4 is reacted in the presence of bases, such as, for example, the alkali salts of lower alcohols, but preferably sodium methylate, with a trialkylphosphonoacetate, such as, for example, triethylphosphonoacetate or trimethylphosphonoacetate in a solvent or solvent mixture. As solvents, lower, preferably primary alcohols, as well as ethers, for example methyl tert-butyl ether, or tetrahydrofuran and mixtures thereof, can be used. Preferred is the use of ethanol. The reaction is performed in a temperature range of 0° C. to 100° C., but preferably in a temperature range of 20° C. to 80° C.

Starting from a compound of formula 4, a compound of formula 5 can also be produced via condensation with Meldrum's acid or malonic acid esters, then saponification and decarboxylation and esterification.

It is familiar to one skilled in the art that $R^1$ can be varied in compounds of formula 5 according to standard methods. This can happen by using other alcohols in the esterification step, but also by reesterification of an already present ester. $R^1$ can thus have the meaning of hydrogen, methyl, ethyl, propyl, isopropyl, butyl, and the corresponding butyl isomers, pentyl and the corresponding pentyl isomers as well as hexyl and the corresponding hexyl isomers, phenyl, benzyl, ortho-, meta- and para-methylphenyl.

The reaction of a ketone of formula 5 in the corresponding 3-alcohol of formula 6 can be performed with a considerable number of reducing agents. As examples, there can be mentioned: $BH_3$ complexes (e.g., with tert-butylamine or trimethylamine), selectrides, sodium and lithium borohydride, inhibited lithium aluminum hydrides (e.g., $LiAl(O'Bu)_3H$); microorganisms such as, e.g., baker's yeasts or enzymes, for example 3β-hydroxysteroid dehydrogenase, can also be used.

It is known to one skilled in the art that depending on the reagent that is used, various solvents or solvent mixtures and reaction temperatures are used. Preferred here, however, are borohydrides, such as, for example, sodium borohydride, in suitable solvents, such as, for example, lower alcohols or mixtures of alcohols with other solvents, for example dichloromethane, tetrahydrofuran or water. The reactions are performed in a temperature range of –20° C. to 40° C., but preferably in the range of –10° C. to 10° C.

The reduction of the 17-double bond in the compounds of general formula 6 is possible according to processes that are known in the art. In this case, two fundamentally different processes can be used.

In this connection, in a way that is similar to reactions that are known in the literature (Synthesis 1996, 455), a suitable reducing agent is a mixture of alkaline-earth metals in lower alcohols. For example, a compound of general formula 6 is reacted in a lower alcohol, preferably methanol, with an alkaline-earth metal, preferably magnesium. The reaction is performed in a temperature range of 0° C. to 80° C., but preferably in a temperature range of 20° C. to 50° C.

As a further reduction process, in this case the catalytic hydrogenation is presented. For example, a compound of formula 6 is hydrogenated in the presence of a suitable catalyst, such as, for example, noble metals or oxides thereof, but preferably platinum oxide. As solvents, lower alcohols, preferably ethanol, as well as ethers, for example methyl tert-butyl ether, or tetrahydrofuran or mixtures thereof, can be used. Preferred is the use of tetrahydrofuran. In this case, surprisingly enough, the 5,6-double bond is not hydrogenated.

The addition of catalytic amounts of acid, such as, for example, sulfuric acid, phosphoric acid or citric acid, has proven advantageous. Preferred is the use of phosphoric acid. The reaction is performed in a temperature range of 10° C. to 100° C.; it can be performed both under normal pressure and under increased pressure. Preferred in this connection is the reaction in the temperature range of 20° C. to 50° C. and under normal pressure.

The introduction of the 7,8-double bond and the isomerization of the double bonds to the double-bond system that is established in the target compound can be achieved in a single-pot process by bromination/dhydrobromination/isomerization (this is also the method using the corresponding chloride and dehydrochlorination).

First, bromination is done with allyl to form the 5,6-double bond in 7-position, and then by thermal elimination of hydrogen bromide, the 5,7-double bond system is obtained, which turns into the desired double-bond system by acidic isomerization. The addition of acid is not necessary; the hydrogen bromide that is formed in the meantime takes over this object in a satisfactory manner.

The bromination is done according to processes that are known in the art. For example, N-bromosuccinimide or N,N-dibromodimethylhydantoin can be used in a suitable solvent, such as, for example, benzene, lower alkanes or else halogenated hydrocarbons, such as, for example, carbon tetrachloride. Solvents other than those previously mentioned, for example methyl formate, can also be used, however (e.g., Angew. Chem. [Applied Chemistry] 1980, 92, 471).

Preferred is the use of heptane as a solvent. The reaction is performed in a temperature range of 30° C. to 130° C., but preferably in a temperature range of 60° C. to 100° C.

EXAMPLES a) 4,4-Dimethylandrostenedione (4)

411 g of potassium tert-butylate is added at room temperature to 500 g of androstenedione in 5 l of tert-butanol. Then, 229 ml of methyl iodide is added in drops, and the mixture is stirred for 1 more hour. For working-up, 400 ml of 1 M $H_2SO_4$ and then 2 l of water are added. The precipitate is filtered off and recrystallized from ethanol. 413 g of 4,4-dimethylandrostenedione is obtained.

$^1$H-NMR (CDCl$_3$): δ=0.89 and 0.90 (2 s, 3H, 18- and 19-H$_3$), 1.06–2.66 (m, 17H, androstenedione), 1.25 [s, 6H, 4-(CH$_3$)$_2$], 5.58–5.61 (m, 1H, 6-H). Melting point: 165–167° C., Combustion analysis: Cld. C, 80.21; H, 9.62; Fnd. C, 79.96; H, 9.61;

b) (20E)-4,4-Dimethyl-3-oxopregna-5,17-diene-21-carboxylic Acid Ethyl Ester (5)

837 ml of 20% sodium ethylate solution and 387 ml of triethylphosphonoacetate are added to 310 g of 4,4-dimethylandrostenedione in 818 ml of ethanol. The mixture is refluxed for 5 hours, then the reaction is completed by adding 1.6 l of water. The precipitate is filtered off, rewashed and dried. 369 g of (20E)-4,4-dimethyl-3-oxopregna-5,17-dien-21-oic acid ethyl ester is obtained.

$^1$H-NMR (CDCl$_3$): δ=0.85 and 0.88 (2 s, 3H, 18- and 19-H$_3$), 1.02–2.91 (m, 17H, androstenedione), 1.26 [s, 6H, 4-(CH$_3$)$_2$], 1.29 (t, 3H, J=7.0, CO$_2$CH$_2$CH$_3$), 4.15 (q, 2H, J=7.1, CO$_2$CH$_2$CH$_3$), 5.55–5.58 (m, 2H, 6-H and 20-H); Melting point: 136–138° C.

c) (20E)-4,4-Dimethyl-3β-hydroxy-pregna-5,17-diene-21-carboxylic Acid-ethyl Ester (6)

200 g of the compound that is described in stage b) is introduced into 2 l of ethanol and mixed with 20 g of sodium borohydride in 0.4 l of water at 0° C. Then, it is stirred for 11 hours. A solution of 328 g of citric acid in 2.8 l of water is added to the reaction mixture, and after 1 hour, the solid is separated. The residue is washed several times with water and dried in a vacuum. 190 g of (20E)-4,4-dimethyl-3β-hydroxy-pregna-5,17-dien-21-oic acid ethyl ester results, which is further used without purification.

$^1$H-NMR (CDCl$_3$): δ=0.83, 1.08, 1.10 and 1.15 [4 s, 3H, 4-(CH$_3$)$_2$, 18- and 19-H$_3$], 0.91–2.90 (m, 17H, androstenedione), 1.28 (t, 3H, J=7.1, CO$_2$CH$_2$CH$_3$), 3.24 (dd to 1H, J=10.2, 5.5, 3-H), 4.15 (q, 2H, J=7.1, CO$_2$CH$_2$CH$_3$), 5.53–5.59 (m, 2H, 6-H and 20-H). Melting point: 171–173° C., Combustion analysis: Cld. C, 77.68; H, 9.91; Fnd. C, 77.75; H, d) 4,4-Dimethyl-3β-hydroxy-pregn-5-ene-21-carboxylic Acid Ethyl Ester (7) (By Hydrogenation)

200 g of (20E)-4,4-dimethyl-3β-hydroxy-pregna-5,17-diene-21-carboxylic acid ethyl ester is dissolved in 1.2 L of THF and mixed with 0.4 ml of 85% phosphoric acid and 4 g of platinum oxide. Then, the reaction vessel is gassed with hydrogen (1 bar). After the hydrogen absorption is completed, catalyst is filtered out, and the solvent is distilled off. 210 g of 4,4-dimethyl-3β-hydroxy-pregn-5-en-21-oic acid ethyl ester results, which is further used without purification.

4,4-Dimethyl-3β-hydroxy-pregn-5-ene-21-carboxylic Acid Ethyl Ester (7) (By Magnesium Reduction)

5.0 g of (20E)-4,4-dimethyl-3β-hydroxy-pregna-5,17-dien-21-oic acid ethyl ester is dissolved at room temperature in 100 ml of methanol and mixed with 0.5 ml of acetic acid. Then, magnesium chips are added in portions to the mixture. After 2.5 hours, it is acidified with 25 ml of acetic acid and then mixed with 200 ml of water. The precipitate is filtered off, rewashed with water and dried. 4.7 g of 4,4-dimethyl-3β-hydroxy-pregn-5-en-21-oic acid ethyl ester results, which is further used without purification.

$^1$H-NMR (CDCl$_3$): δ=0.61, 1.08, 1.10 and 1.15 [4 s, 3H, 4-(CH$_3$)$_2$, 18- and 19-H$_3$), 0.90–2.42 (m, 18H, androstenedione), 1.25 (t, 3H, J=7.1, CO$_2$CH$_2$CH$_3$), 3.22–3.26 (m, 1H, 3-H), 4.11 (q, 2H, J=7.1, CO$_2$CH$_2$CH$_3$), 5.55–5.58 (m, 1H, 6-H) Melting point: 127–129° C., Combustion analysis: Cld. C, 77.27; H, 10.38; Fnd. C, 77.00; H, 10.20.

e) 4,4-Dimethyl-3β-hydroxypregna-8,14-diene-21-carboxylic Acid Ethyl Ester (1)

100 g of the compound that is described in stage d) is refluxed for 20 hours with 48 g of 1,3-dibromo-5,5-dimethylhydantoin in 2.5 l of n-heptane. After cooling, the mixture is extracted with ethyl acetate, the organic phase is washed several times with water and concentrated by evaporation. 50 g of 4,4-dimethyl-3β-hydroxypregna-8,14-dien-21-oic acid ethyl ester is obtained.

$^1$H-NMR (CDCl$_3$): δ=0.75, 0.83, 1.02 and 1.03 [4 s, 3H, 4-(CH$_3$)$_2$, 18- and 19-H$_3$], 0.62–2.59 (m, 17H, androstenedione), 1.26 (t, 3H, J=7.1, CO$_2$CH$_2$CH$_3$), 3.25 (dd, 1H, J=11.4, 4.8, 3-H), 4.13 (q, 2H, J=7.1, CO$_2$CH$_2$CH$_3$), 5.35 (br. s, 1H, 15-H); MS (Cld. 386.58): .M+-Peak at 387.

Further processing to form 4,4-dimethyl-5α-cholesta-8,14,24-trien-3β-ol (2) (FF-MAS):

f) Beginning With 4,4-Dimethyl-3β-hydroxypregna-8,14-dien-21-oic Acid Methyl Ester further to form g) 4,4-Dimethyl-3β-[[dimethyl(1,1-dimethylethyl)-silyl]oxy]pregna-8,14-dien-21-oic Acid Methyl Ester 92 g of 4,4-dimethyl-3β-hydroxypregna-8,14-dien-21-oic acid methyl ester is stirred with 0.75 liter of N,N-dimethylformamide, 51 g of tert-butyldimethylsilyl chloride and 27.8 g of imidazole for 18 hours at 70° C. After cooling, it is poured into 10 liters of an ice-cold 0.5 molar aqueous hydrochloric acid and filtered. The filter cake is taken up in ethyl acetate, washed neutral with 1N sodium hydroxide solution, dried on sodium sulfate, filtered and concentrated by evaporation. 124.8 g of 4,4-dimethyl-3β-[[dimethyl(1,1-dimethylethyl)silyl]oxy]pregna-8,14-dien-21-oic acid methyl ester is obtained, which is further used without purification.

h) 4,4-Dimethyl-3β-[[dimethyl(1,1-dimethylethyl)silyl]oxy]-5β-cholesta-8,14,24-trien-21-oic Acid Methyl Ester 123.5 g of the compound that is described in stage b), dissolved in 2.0 liters of tetrahydrofuran, is added in drops at −20° C. to a solution of 1.04 mol of lithium diisopropylamide, produced from 652 ml of a 1.6 molar solution of n-butyllithium in hexane and 174 ml of diisopropylamine in 320 ml of tetrahydrofuran. After 40 minutes of stirring at 0° C., it is cooled to −10° C., and 270 g of 5-iodo-2-methyl-2-pentene is added in drops. After 3 hours of stirring at 0° C., the batch is dispersed between ethyl acetate and saturated ammonium chloride solution. After the organic phase is washed with water and saturated common salt solution, drying on sodium sulfate and filtration, it is concentrated by evaporation and filtered coarsely over silica gel with a mixture that consists of n-hexane and ethyl acetate. 113 g (0.2 mol) of 4,4-dimethyl-3β-[[dimethyl(1,1-dimethylethyl)-silyl]oxy]-5α-cholesta-8,14,24-trien-21-oic acid methyl ester is obtained, which is further used without purification.

i) 4,4-Dimethyl-3β-[[dimethyl(1,1-dimethylethyl)silyl]oxy]-5α-cholesta-8,14,24-trien-21-ol 112.5 g of the compound that is described in stage c), dissolved in 0.7 liter of tetrahydrofuran, is added in drops at 0° C. to 15.04 g of lithium aluminum hydride, suspended in 0.7 liter of tetrahydrofuran. After 3 hours of stirring at room temperature, it is mixed with 60 ml of saturated ammonium chloride solution while being cooled with ice. After 20 minutes of stirring, it is mixed with sodium sulfate, and after another 10 minutes, it is suctioned off. The evaporation residue is filtered on a short column with dichloromethane as a solvent. After the eluate is concentrated by evaporation, 103.2 g of 4,4-dimethyl-3β-[[dimethyl(1,1-dimethylethyl)silyl]oxy]-5α-cholesta-8,14,24-trien-21-ol is obtained, which is further used without further purification.

j) 4,4-Dimethyl-3β-[[dimethyl(1,1-dimethylethyl)silyl]oxy]-5α-cholesta-8,14,24-trien-21-ol-methanesulfonate At 0° C., 21.8 ml of methanesulfonic acid chloride is added in drops to a solution of 102.3 g of the compound that is described in stage d) in a mixture that consists of 440 ml of dichloromethane and 84 ml of triethylamine. After 3 hours at room temperature, it is dispersed between water and dichloromethane. After the organic phase is washed with sodium bicarbonate solution, saturated common salt solution, drying on sodium sulfate, filtration and concentration by evaporation, it is chromatographed on silica gel with a mixture that consists of hexane and ethyl acetate. 78.2 g of 4,4-dimethyl-3β-[[dimethyl(1,1-dimethylethyl)silyl]oxy]-5α-cholesta-8,14,24-trien-21-ol-methanesulfonate is obtained.

k) 4,4-Dimethyl-3β-[[dimethyl(1,1-dimethylethyl)silyl]oxy]-5α-cholesta-8,14,24-triene 77.2 g of the compound that is described in stage e) is reacted according to the method that is described in stage d).

After the crude product is filtered on silica gel with a mixture that consists of n-hexane and ethyl acetate, 63 g of 4,4-dimethyl-3β-[[dimethyl(1,1-dimethylethyl)silyl]oxy]-5α-cholesta-8,14,24-triene is obtained.

1) 4,4-Dimethyl-5α-cholesta-8,14,24-trien-3β-ol 2 g of the compound that is described in stage f) is stirred in a mixture that consists of 5 ml of 6N hydrochloric acid, 10 ml of ethanol and 30 ml of tetrahydrofuran for 24 hours at room temperature. Then, it is dispersed between ethyl acetate and water. After the organic phase is washed with 1N sodium hydroxide solution, water and saturated common salt solution, drying on sodium sulfate and filtration, the evaporation residue is chromatographed on silica gel with a mixture that consists of n-hexane and ethyl acetate.

1.45 g of 4,4-dimethyl-5α-cholesta-8,14,24-trien-3β-ol is obtained.

The NMR data are identical to those of the literature (J. Am. Chem. Soc. 111, 1989, 278)

What is claimed is:

1. A process for the production of 4,4-dimethyl-3β-hydroxypregna-8,14-diene-21-carboxylic acid esters of formula I

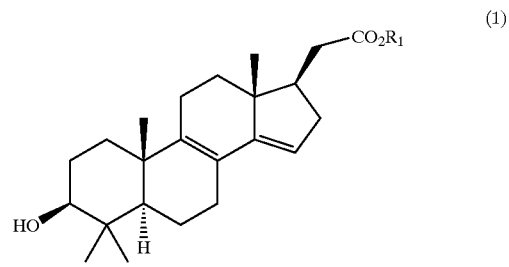

in which $R^1$=hydrogen, branched or unbranched $C_1$–$C_6$ alkyl, phenyl, benzyl, ortho-, meta- or para-methylphenyl, by (a) dimethylating androstenedione 3

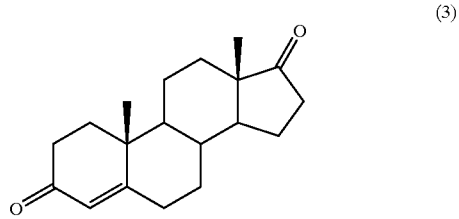

(a) into 4,4-dimethylandrostenedione of formula 4

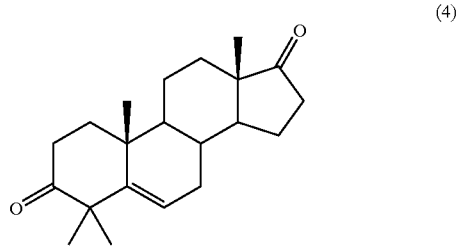

(b) alkylating (4) into a 4,4-dimethyl-3-oxopregna-5,17-diene-21-carboxylic acid ester of formula 5

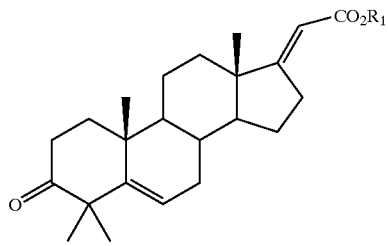

in which
R¹=hydrogen, branched or unbranched $C_1$–$C_6$ alkyl, phenyl, benzyl, ortho-, meta- or para-methylphenyl, (c) reducing (5) into a 4,4-dimethyl-3β-hydroxy-pregna-5,17-diene-21-carboxylic acid ester of formula 6

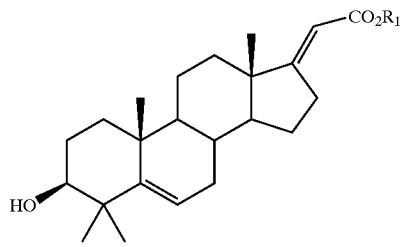

in which
R¹=hydrogen, branched or unbranched $C_1$–$C_6$ alkyl, phenyl, benzyl, ortho-, meta- or para-methylphenyl, (d) reducing the 17-double bond of (6) into a 4,4-dimethyl-3β-hydroxy-pregn-5-ene-21-carboxylic acid ester of formula 7

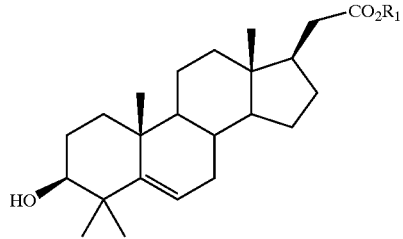

in which
R¹=hydrogen, branched or unbranched $C_1$–$C_6$ alkyl, phenyl, benzyl, ortho-, meta- or para-methylphenyl,
and subsequently halogenating, dehydrohalogenating, isomerizing and converting into the 4,4-dimethyl-3β-hydroxypregna-8,14-diene-21-carboxylic acid ester of formula (1).

2. A 4,4-Dimethyl-3-oxopregna-5,17-diene-21-carboxylic acid ester of formula 5

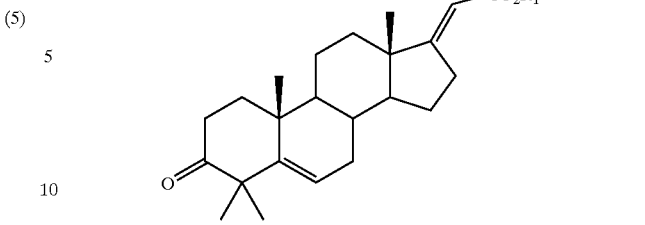

in which
R¹=hydrogen, branched or unbranched $C_1$–$C_6$ alkyl, phenyl, benzyl, ortho-, meta- or para-methylphenyl.

3. A 4,4-Dimethyl-3β-hydroxy-pregna-5,17-diene-21-carboxylic acid ester of formula 6

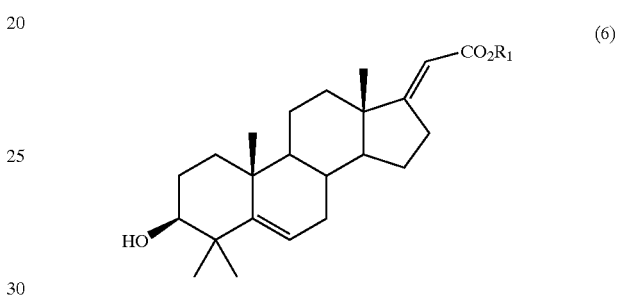

in which
R¹=hydrogen, branched or unbranched $C_1$–$C_6$ alkyl, phenyl, benzyl, ortho-, meta- or para-methylphenyl.

4. A process for making an intermediate in the production of FF-MAS, comprising dimethylating androstenedione 3

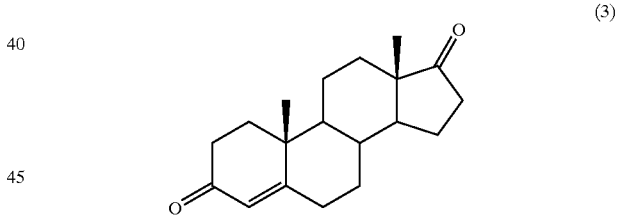

to produce a starting material a compound of formula 1

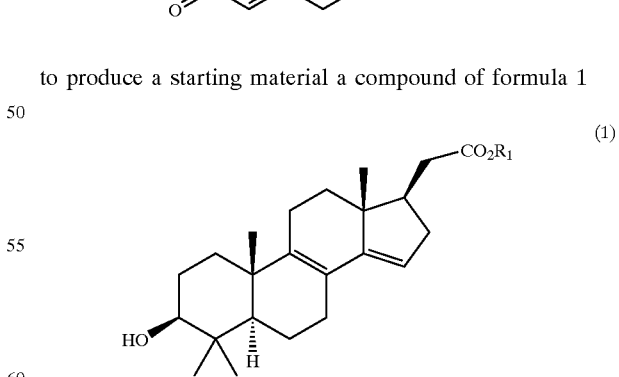

in which R¹=hydrogen, branched or unbranched $C_1$–$C_6$ alkyl, phenyl, benzyl, ortho-, meta- or para-methylphenyl.

5. A process for making an intermediate in the production of FF-MAS, comprising alkylating a compound of formula 4

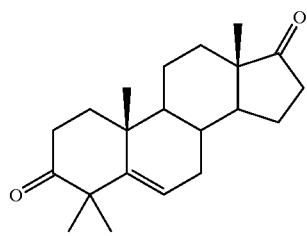 (4)

into a compound of formula 5

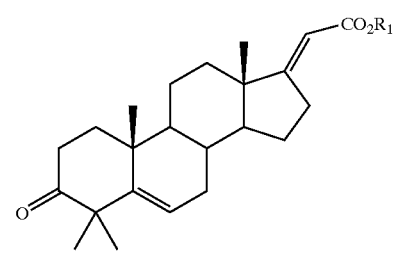 (5)

wherein $R^1$=hydrogen, branched or unbranched $C_1$–$C_6$ alkyl, phenyl, benzyl, ortho-, meta- or para-methylphenyl, and reducing the compound of formula (5) to a compound of formula (6)

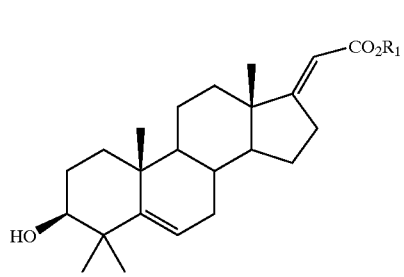 (6)

6. A process for the production of an intermediate in the production of FF-MAS, comprising reducing a compound of formula (5),

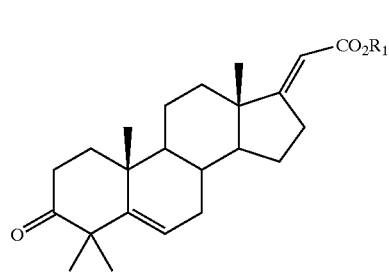 (5)

wherein $R^1$=hydrogen, branched or unbranched $C_1$–$C_6$ alkyl, phenyl, benzyl, ortho-, meta- or para-methylphenyl to a compound of formula (6)

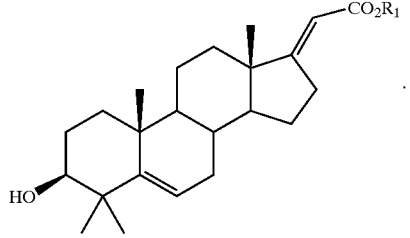 (6)

7. A process for the production of an intermediate in the production of FF-MAS, comprising alkylating a compound of formula 4

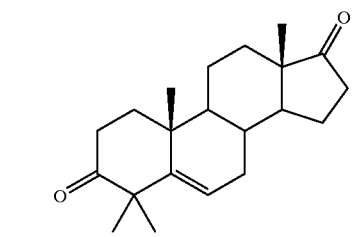 (4)

into a compound of formula 5

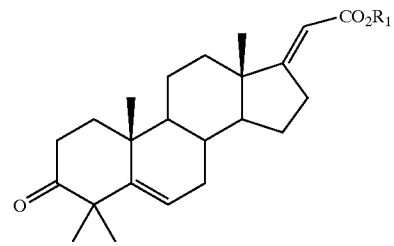 (5)

wherein $R^1$=hydrogen, branched or unbranched $C_1$–$C_6$ alkyl, phenyl, benzyl, ortho-, meta- or para-methylphenyl.

* * * * *

UNITED STATES PATENT AND TRADEMARK OFFICE
CERTIFICATE OF CORRECTION

PATENT NO. : 6,653,491 B1
DATED : November 25, 2003
INVENTOR(S) : Geisler et al.

It is certified that error appears in the above-identified patent and that said Letters Patent is hereby corrected as shown below:

<u>Title page,</u>
Item [56], References Cited, OTHER PUBLICATIONS,
"R E Dolle et al.," reference reads "Oktober," should read -- October --

<u>Column 8,</u>
Line 53, delete "(a)"

<u>Column 10,</u>
Line 49, reads, "material a compound," should read -- material compound --

Signed and Sealed this

Seventeenth Day of August, 2004

JON W. DUDAS
*Acting Director of the United States Patent and Trademark Office*